United States Patent
Palackal et al.

(10) Patent No.: US 11,782,023 B2
(45) Date of Patent: Oct. 10, 2023

(54) CE-WESTERN APPLICATIONS FOR ANTIBODY DEVELOPMENT

(71) Applicant: Regeneron Pharmaceuticals, Inc., Tarrytown, NY (US)

(72) Inventors: Nisha Palackal, White Plains, NY (US); Kun Lu, Scarsdale, NY (US); Gangadhar Dhulipala, White Plains, NY (US); Erica Pyles, New City, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 766 days.

(21) Appl. No.: 16/716,734

(22) Filed: Dec. 17, 2019

(65) Prior Publication Data
US 2020/0200707 A1    Jun. 25, 2020

Related U.S. Application Data

(60) Provisional application No. 62/781,790, filed on Dec. 19, 2018.

(51) Int. Cl.
| G01N 27/447 | (2006.01) |
| G01N 33/543 | (2006.01) |
| G01N 33/558 | (2006.01) |

(52) U.S. Cl.
CPC . *G01N 27/44726* (2013.01); *G01N 27/44743* (2013.01); *G01N 27/44795* (2013.01); *G01N 33/54306* (2013.01); *G01N 33/558* (2013.01)

(58) Field of Classification Search
CPC ....... G01N 27/44726; G01N 27/44743; G01N 27/44795; G01N 33/54306; G01N 33/558
See application file for complete search history.

(56) References Cited

U.S. PATENT DOCUMENTS

| 2009/0023156 A1* | 1/2009 | Voss ................. G01N 33/54366 |
| | | 435/7.1 |
| 2010/0331527 A1* | 12/2010 | Davis .................. C07K 16/2887 |
| | | 435/69.6 |
| 2017/0045527 A1* | 2/2017 | Muthusamy ......... C07K 16/468 |

FOREIGN PATENT DOCUMENTS

WO    WO2000/50172 A1    8/2000

OTHER PUBLICATIONS

Antibody—Wikipedia (Year: 2022).*
06-182_2459609 Upstate. (Year: 2022).*
(Continued)

*Primary Examiner* — Caitlyn Mingyun Sun
(74) *Attorney, Agent, or Firm* — Kramer Levin Naftalis & Frankel LLP

(57) ABSTRACT

Methods for detecting and/or discriminating between variants of an antibody contaminating protein or multiple antibodies in a sample by a physical parameter, in which the method includes: separating protein components of a sample by molecular weight or charge in one or more capillaries using capillary electrophoresis; immobilizing the protein components of the sample within the one or more capillaries; contacting the protein components within the one or more capillaries with one or more primary antibodies that specifically bind to the antibody, the contaminating protein or multiple antibodies in the sample, thereby detecting and/or discriminating between variants in the sample.

18 Claims, 13 Drawing Sheets
(13 of 13 Drawing Sheet(s) Filed in Color)

Size-based Assay

(56) References Cited

OTHER PUBLICATIONS

Richard R. Rustandi et al.: "Qualitative and quantitative evaluation of Simon(TM), a new CE-based automated Western blot system as applied to vaccine development: CE and CEC", Electrophoresis, vol. 33, No. 17, Sep. 1, 2012 (Sep. 1, 2012), pp. 2790-2797.
Wang Jinyu et al.: "Evaluation of automated Wes system as an analytical and characterization tool to support monoclonal antibody drug product development," Journal of Pharmaceutical and Biochemical Analysis, Elsevier B.V, Amsterdam, NL, vol. 139, Dec. 21, 2016 (Dec. 21, 2016), pp. 263-268.
O'Neill Roger A et al: "Isoelectric focusing technology quantifies protein signaling in 25 cells", Proceedings of the National Academy of Sciences, National Academy of Sciences, US, vol. 103, No. 44, Oct. 31, 2006 (Oct. 31, 2006), pp. 16153-16158.
European Search Report Applicaiton No. 19218272.3, dated May 4, 2020.

\* cited by examiner

CE-WESTERN APPLICATIONS FOR ANTIBODY DEVELOPMENT

FIELD OF THE INVENTION

The present invention pertains to biopharmaceuticals, and relates to the use of capillary electrophoresis to detect biopharmaceuticals and contaminants in complex mixtures.

BACKGROUND

Monoclonal antibodies (mAbs) are a significant class of biotherapeutic products, and they have achieved outstanding success in treating many life-threatening and chronic diseases. However, mAbs are also highly complex biological macromolecules with size and charge variants, various post translational modifications, including different glycosylation patterns, and N and C terminal heterogeneity. Each individual monoclonal antibody may therefore present a unique profile, a characteristic, which needs to be taken into consideration during the evaluation of these products both during development and during manufacturing of final product.

Monitoring and evaluation of critical quality attributes (CQA) in mAbs are a regulatory requirement in the pharmaceutical industry. During mAb production, the presence of potentially contaminating proteins must also be considered. In addition, as the use of combination therapies grows (for example the use of multiple mAbs in drug product cocktails) the ability to monitor the individual mAbs in these cocktails will also become increasingly important.

Electrophoresis has been used for separating mixtures of molecules based on their different rates of travel in electric fields. Generally, electrophoresis refers to the movement of suspended or dissolved molecules through a fluid or gel under the action of an electromotive force applied to one or more electrodes or electrically conductive members in contact with the fluid or gel. Some known modes of electrophoretic separation include separating molecules based, at least in part, on differences in their mobilities in a buffer solution (commonly referred to as zone electrophoresis), in a gel or polymer solution (commonly referred to as gel electrophoresis), or in a potential of hydrogen (pH) gradient (commonly referred to as isoelectric focusing). Even though capillary electrophoresis techniques are effective and widely used in the industry to study biomolecule purity and charge heterogeneity, it does not allow selective detection of various species or allow differentiation of product and process impurities. Accordingly, additional methods of monitoring mAb preparations and formulations are needed.

SUMMARY OF THE INVENTION

In one aspect, the present invention provides a method for detecting and/or discriminating between variants of an antibody in a sample by a physical parameter, in which the method includes: separating protein components of a sample comprising an antibody of interest by molecular weight or charge in one or more capillaries using capillary electrophoresis; immobilizing the protein components of the sample within the one or more capillaries; contacting the protein components within the one or more capillaries with one or more primary antibodies that specifically bind to the, protein, such as an antibody, of interest, or part thereof; and detecting the binding of the one or more primary antibodies, thereby detecting and/or discriminating between size variants of the antibody of interest in the sample.

In various embodiments of the method, the one or more primary antibodies comprise at least one antibody that specifically binds a heavy chain of the antibody of interest.

In various embodiments of the method, the one or more primary antibodies comprise at least one antibody that specifically binds a light chain of the antibody of interest.

In various embodiments of the method, the one or more primary antibodies are labeled with a detectable label, and detecting the binding of the one or more primary antibodies includes detecting the detectable label.

In various embodiments of the method, detecting the binding of the one or more primary antibodies includes: contacting the one or more primary antibodies with a secondary antibody that specifically binds at least one of the one or more primary antibodies, wherein the secondary antibody has a detectable label; and detecting the detectable label.

In various embodiments of the method, the protein components of a sample are separated by charge and the method is a method of detecting and/or discriminating between charge variants of the antibody of interest.

In various embodiments of the method, the protein components of a sample are separated by molecular weight and the method is a method of detecting and/or discriminating between size variants of the antibody interest.

In various embodiments of the method, the sample comprises one or more additional antibodies of interest.

In various embodiments of the method, the one or more additional antibodies of interest are detected.

In some embodiments, the method further includes determining a relative or absolute amount of the variants of the antibody in a sample.

In various embodiments of the method, the antibody of interest comprises a bispecific antibody.

In various embodiments of the method, the detectable label comprises a chemiluminescent, a fluorescent label or a bioluminescent label.

In various embodiments of the method, the sample includes an internal standard.

In various embodiments of the method, immobilizing comprises photo-immobilizing, chemically immobilizing, or thermally immobilizing.

In various embodiments of the method, the one or more capillaries comprise a separation matrix.

In various embodiments of the method, the separation matrix comprises carrier ampholytes.

In various embodiments of the method, the separation matrix comprises a sieving matrix configured to separate proteins by molecular weight.

In one aspect, the present invention provides a method for detecting protein contaminants of interest in an antibody preparation sample, in which the method includes: separating protein components of a sample by a physical parameter in one or more capillaries using capillary electrophoresis; immobilizing the protein components of the sample within the one or more capillaries; contacting the protein components within the one or more capillaries with one or more primary antibodies that specifically bind to a protein contaminant of interest; and detecting the binding of the one or more primary antibodies, thereby detecting protein contaminants of interest in the antibody preparation sample.

In some embodiments, the method further includes discriminating between variants of the protein contaminant of interest in the antibody preparation sample by the physical parameter.

In various embodiments of the method, the one or more capillaries comprise a separation matrix.

In various embodiments of the method, the separation matrix comprises carrier ampholytes.

In various embodiments of the method, the physical parameter comprises charge.

In various embodiments of the method, the separation matrix comprises a sieving matrix configured to separate proteins by molecular weight.

In various embodiments of the method, the physical parameter comprises molecular weight.

In various embodiments of the method, the one or more primary antibodies are labeled with a detectable label, wherein detecting the binding of the one or more primary antibodies comprises detecting the detectable label.

In various embodiments of the method, detecting the binding of the one or more primary antibodies further includes: contacting the one or more primary antibodies with a secondary antibody that specifically binds at least one of the one or more primary antibodies, and wherein the secondary antibody has a detectable label; and detecting the detectable label.

In some embodiments, the method further includes detecting and/or discriminating between charge or size variants of the protein contaminants of interest.

In some embodiments, the method further includes determining a relative or absolute amount of the protein contaminants of interest.

In various embodiments of the method, the detectable label comprises a chemiluminescent, a fluorescent label or a bioluminescent label.

In various embodiments of the method, the sample includes an internal standard.

In various embodiments of the method, immobilizing comprises photo-immobilizing, chemically immobilizing, or thermally immobilizing.

In various embodiments of the method, the one or more primary antibodies comprise polyclonal antibodies.

In various embodiments of the method, the protein contaminants of interest comprise PLBD2.

In another aspect, the present invention provides a method for detecting and/or discriminating between antibodies in a mixture of two of more antibodies in a sample by a physical parameter, in which the method includes: separating protein components of a sample comprising two or more antibodies of interest by charge in one or more capillaries using capillary electrophoresis; immobilizing the protein components of the sample within the one or more capillaries; contacting the protein components within the one or more capillaries with a first primary antibody that specifically binds to a first antibody of interest; detecting the binding of the first primary antibody, thereby detecting the first antibody of interest; contacting the protein components within the one or more capillaries with a second primary antibody that specifically binds to a second antibody of interest; and detecting the binding of the second primary antibody, thereby detecting the second antibody of interest and discriminating between the antibodies in a sample.

In some embodiments, the method further includes contacting the protein components within the one or more capillaries with a third primary antibody that specifically binds to a third antibody of interest; detecting the binding of the a third primary antibody, thereby detecting the third antibody of interest.

In some embodiments, the method further includes contacting the protein components within the one or more capillaries with one or more additional primary antibodies that specifically binds to one or more additional antibodies of interest; and detecting the binding of the one or more additional primary antibodies, thereby detecting the additional antibodies of interest.

In various embodiments of the method, the primary antibodies are labeled with a detectable label, and wherein detecting the binding of the primary antibodies comprises detecting the detectable label.

In various embodiments of the method, detecting the binding of the primary antibodies comprises: contacting the primary antibodies with a secondary antibody that specifically binds the primary antibodies, and wherein the secondary antibody has a detectable label; and detecting the detectable label.

In some embodiments, the method further includes determining a relative or absolute amount of the antibodies of interest in the mixture.

In various embodiments of the method, the detectable label comprises a chemiluminescent, a fluorescent label, or a bioluminescent label.

In various embodiments of the method, the sample includes an internal standard.

In various embodiments of the method, immobilizing comprises photo-immobilizing, chemically immobilizing, or thermally immobilizing.

In various embodiments of the method, the one or more capillaries comprise a separation matrix.

In various embodiments of the method, the separation matrix comprises carrier ampholytes.

In various embodiments, any of the features or components of embodiments discussed above or herein may be combined, and such combinations are encompassed within the scope of the present disclosure. Any specific value discussed above or herein may be combined with another related value discussed above or herein to recite a range with the values representing the upper and lower ends of the range, and such ranges are encompassed within the scope of the present disclosure.

DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
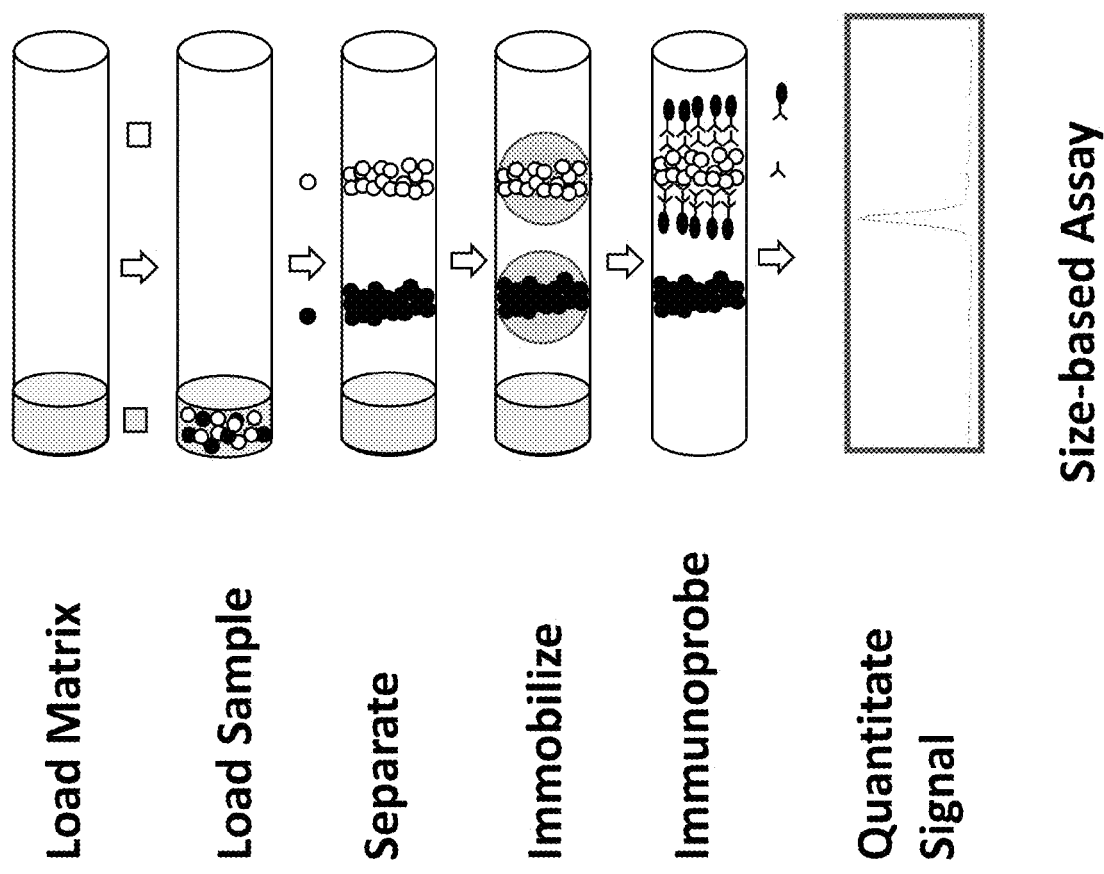
FIG. 1 is a diagram of an exemplary work flow for the separation and detection of proteins by capillary electrophoresis by approximate molecular weight.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims. Any embodiments or features of embodiments can be combined with one another, and such combinations are expressly encompassed within the scope of the present invention.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.)

Although any methods and materials similar or equivalent to those described herein can be used in the practice or testing of the present invention, the preferred methods and materials are now described. All patents, applications and non-patent publications mentioned in this specification are incorporated herein by reference in their entireties.

Abbreviations Used Herein
mAb: Monoclonal antibody
biAb: Bispecific antibody
CQA: Critical quality attributes
CE: Capillary Electrophoresis
SDS: Sodium dodecyl sulfate
iCIEF: Imaged CIEF
iCIEF-western; Charged based CE-Western
IEC: Ion exchange chromatography
QC: Quality control
HRP: Horse radish peroxidase
HCPs: Host Cell Proteins
Definitions The term "antibody", as used herein, is intended to refer to immunoglobulin molecules included of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is included of a heavy chain variable region ("HCVR" or "$V_H$") and a heavy chain constant region (included of domains $C_H1$, $C_H2$ and $C_H3$). In various embodiments, the heavy chain may be an IgG isotype. In some cases, the heavy chain is selected from IgG1, IgG2, IgG3 or IgG4. In some embodiments, the heavy chain is of isotype IgG1 or IgG4, optionally including a chimeric hinge region of isotype IgG1/IgG2 or IgG4/IgG2. Each light chain is included of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The term "antibody" includes reference to both glycosylated and non-glycosylated immunoglobulins of any isotype or subclass. The term "antibody" includes antibody molecules prepared, expressed, created or isolated by recombinant means, such as antibodies isolated from a host cell transfected to express the antibody. For a review on antibody structure, see Lefranc et al., *IMGT unique numbering for immunoglobulin and T cell receptor variable domains and Ig superfamily V-like domains*, 27(1) Dev. Comp. Immunol. 55-77 (2003); and M. Potter, *Structural correlates of immunoglobulin diversity*, 2(1) Surv. Immunol. Res. 27-42 (1983).

The term antibody also encompasses a "bispecific antibody", which includes a heterotetrameric immunoglobulin that can bind to more than one different epitope. One half of the bispecific antibody, which includes a single heavy chain and a single light chain and six CDRs, binds to one antigen or epitope, and the other half of the antibody binds to a different antigen or epitope. In some cases, the bispecific antibody can bind the same antigen, but at different epitopes or non-overlapping epitopes. In some cases, both halves of the bispecific antibody have identical light chains while retaining dual specificity. Bispecific antibodies are described generally in U.S. Patent App. Pub. No. 2010/0331527 (Dec. 30, 2010).

The term "antigen-binding portion" of an antibody (or "antibody fragment"), refers to one or more fragments of an antibody that retain the ability to specifically bind to an antigen. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) Nature 241:544-546), which consists of a VH domain, (vi) an isolated CDR, and (vii) an scFv, which consists of the two domains of the Fv fragment, VL and VH, joined by a synthetic linker to form a single protein chain in which the VL and VH regions pair to form monovalent molecules. Other forms of single chain antibodies, such as diabodies are also encompassed under the term "antibody" (see e.g., Holliger et at. (1993) 90 PNAS U.S.A. 6444-6448; and Poljak et at. (1994) 2 Structure 1121-1123).

Moreover, antibodies and antigen-binding fragments thereof can be obtained using standard recombinant DNA techniques commonly known in the art (see Sambrook et al., 1989).

The term "human antibody", is intended to include antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences. The term includes antibodies recombinantly produced in a non-human mammal, or in cells of a non-human mammal. The term is not intended to include antibodies isolated from or generated in a human subject.

The term "sample," as used herein, refers to a mixture of molecules that includes at least one polypeptide of interest, such as a monoclonal antibody or a bispecific antibody, that is subjected to manipulation in accordance with the methods of the invention, including, for example, separating, analyzing, extracting, concentrating or profiling.

The terms "analysis" or "analyzing," as used herein, are used interchangeably and refer to any of the various methods of separating, detecting, isolating, purifying, solubilizing, detecting and/or characterizing molecules of interest (e.g., polypeptides, such as antibodies) and contaminants in antibody preparations.

"Chromatography," as used herein, refers to the process of separating a mixture, for example a mixture containing peptides, proteins, polypeptides and/or antibodies, such as monoclonal antibodies. It involves passing a mixture through a stationary phase, which separates molecules of interest from other molecules in the mixture and allows one or more molecules of interest to be isolated. In the method disclosed herein chromatography refers to capillary electrophoresis, including size based capillary electrophoresis and isoelectric focusing or charged based capillary electrophoresis.

"Contacting," as used herein, includes bringing together at least two substances in solution or solid phase, for example contacting a sample with an antibody, such as an antibody that specifically binds to a molecule of interest, such as a therapeutic or potential therapeutic antibody.

The term "isolated," as used herein, refers to a biological component (such as an antibody, for example a monoclonal antibody) that has been substantially separated, produced apart from, or purified away from other biological components in the cell of the organism in which the component naturally occurs or is transgenically expressed, that is, other chromosomal and extrachromosomal DNA and RNA, proteins, lipids, and metabolites. Nucleic acids, peptides, proteins, lipids and metabolites which have been "isolated" thus include nucleic acids, peptides, proteins, lipids, and metabolites purified by standard or non-standard purification methods. The term also embraces nucleic acids, peptides, proteins, lipids, and metabolites prepared by recombinant expression in a host cell as well as chemically synthesized peptides, lipids, metabolites, and nucleic acids.

The terms "peptide," "protein" and "polypeptide" refer, interchangeably, to a polymer of amino acids and/or amino acid analogs that are joined by peptide bonds or peptide bond mimetics. The twenty naturally-occurring amino acids and their single-letter and three-letter designations are as follows: Alanine A Ala; Cysteine C Cys; Aspartic Acid D Asp; Glutamic acid E Glu; Phenylalanine F Phe; Glycine G Gly; Histidine H His; Isoleucine I He; Lysine K Lys; Leucine L Leu; Methionine M Met; Asparagine N Asn; Proline P Pro; Glutamine Q Gln; Arginine R Arg; Serine S Ser; Threonine T Thr; Valine V Val; Tryptophan w Trp; and Tyrosine Y Tyr. In one embodiment a peptide is an antibody or fragment or part thereof, for example, any of the fragments or antibody chains listed above. In some embodiments, the peptide may be post-translationally modified.

"Detect" and "detection" have their standard meaning, and are intended to encompass detection including the presence or absence, measurement, and/or characterization of an protein of interest, such as a mAb or contaminant protein.

As used herein, the terms "protein of interest" and/or "target protein of interest" refer to any protein to be separated and/or detected with the methods, provided herein. Suitable protein of interests include antibodies, for example monoclonal antibodies, and other proteins, such as contaminating proteins in antibody preparations.

As used herein, the terms "standard" and/or "internal standard" refer to a well-characterized substance of known amount and/or identity (e.g., known molecular weight, electrophoretic mobility profile) that can be added to a sample and both the standard and the molecules in the sample, on the basis of molecular weight or isoelectric point by electrophoresis). A comparison of the standard then provides a quantitative or semi-quantitative measure of the amount of analyte, such as mAb or contaminant protein present in the sample.

General Description

Characterization of monoclonal antibody (mAb) variants is important in order to identify their potential impact on safety, potency, and stability of a potential therapeutic antibody. For example, to be considered for approval by regulatory agencies, extensive characterization of the molecule must be performed. In drug products comprising mixtures of antibodies, characterization of the absolute or relative amounts of each antibody must be determined. Because aggregates and fragments may potentially affect immunogenicity and potency, their levels are typically monitored during lot release, stability, and characterization. Furthermore, primary degradation pathways for the molecule and product related impurities and variants are determined. Ion exchange chromatography (IEC) coupled with UV detection is frequently used to separate and quantify mAb variants in routine quality control (QC). However, characterization of the chromatographic peaks resulting from an IEC separation is an extremely time-consuming process. Thus addition methods are needed to characterize potential therapeutic mAbs and potential contaminants of mAb preparations. The methods disclosed herein meet those needs.

Figure 2A:
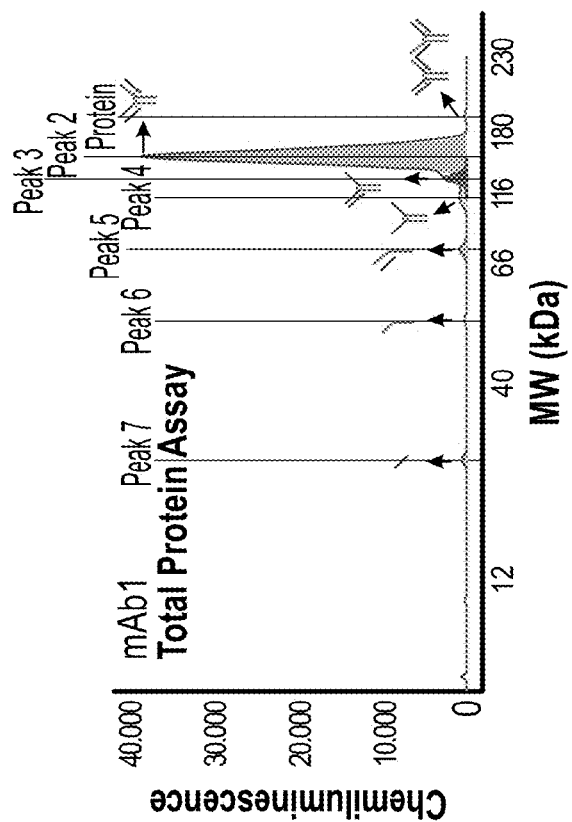
FIG. 2A is a graphed set of traces showing an analysis of antibody fragments by CE-Western using anti Kappa and anti FC antibodies. This result demonstrates that size based CE-western can sensitively quantitate size variants in mAb samples.
Figure 2B:
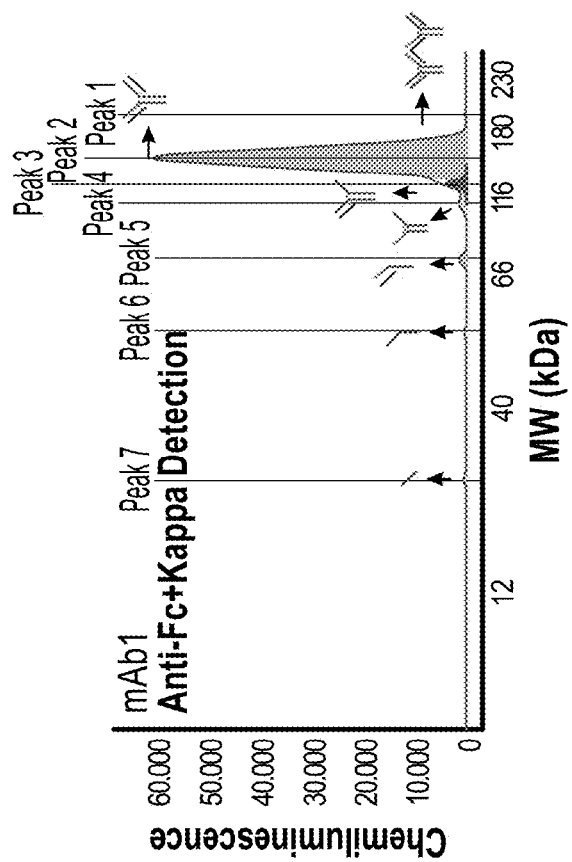
FIG. 2B is a graph showing the analysis of antibody fragments by CE-Western using total protein analysis. This result demonstrates that size based CE-western analysis can sensitively quantitate size variants in mAb samples.

Disclosed herein is a method for detecting and/or discriminating between variants of a monoclonal antibody (mAb) in a sample by a physical parameter, such as the molecular weight or the isoelectric point of the mAb. The disclosed methods can be used in QC evaluation of antibody preparations. In embodiments of the method, a sample that includes a mAb of interest is resolved or separated by using capillary electrophoresis, for example on one or more capillaries of a CE-system. In certain embodiments, the sample is resolved or separated by molecular weight. Resolution by molecular weight allows for the determination of what antibody fragments or species are present in the sample, for example unpaired heavy or light chains in addition to the fully formed mAb (examples of which are shown in FIGS. 2A and 2B). In certain embodiments, the sample is resolved or separated by charge, for example by isoelectric focusing. Separation of the mAb by charge has the added benefit of being able to determine the homogeneity of the mAb, for example, changes in surface charge of the mAb that may not be easy seen in separation by molecular weight. In certain embodiments, the sample is resolved or separated within a single capillary. In certain embodiments, the sample is resolved or separated within multiple capillaries, for example in parallel. Once the protein components have been resolved or separated in the one or more capillaries, the protein components, for example the mAb of interest, are immobilized within the capillary so that the relative positon of the mAb of interest in the one or more capillaries is maintained. In embodiments, the mAb of interest is detected by contacting the protein components within the one or more capillaries, including the mAb of interest, with one or more primary antibodies that specifically bind to the mAb of interest to detect the presence of the mAb of interest. In embodiments, the method includes detecting the binding of the one or more primary antibodies, for example because its mobility in the capillary is impaired by the immobilization of the mAb of interest. Detection of the binding of the primary antibody, for example along the length of a capillary, allows for the detecting of and/or discrimination between size and/or change variants of the mAb of interest in the sample, depending on weather the sample was subjected to separation by mass or charge, respectively. By way of example with respect to separation by molecular weight, the smaller the fragment of a mAb the further within a capillary it would be expected to travel. In embodiments, the sample may contain multiple, such as at least 2, at least 3, at least 4, at least 5 or more mAbs of interest, each of which can be detected using a primary antibody that specifically binds to the individual mAb of interest. In some embodiments, the method further includes determining a relative or absolute amount of the variants of the monoclonal antibody in a sample, for example by measurement of peak height or area, which corresponds to the amount of labeled primary antibody detected and therefore how much mAb of interest is available to bind the labeled primary antibody. In some embodiments, the monoclonal antibody of interest comprises a bispecific monoclonal antibody. In some embodiments, the one or more primary antibodies comprise at least one monoclonal antibody that specifically binds a heavy chain of the antibody of interest. In some embodiments, the one or more primary antibodies comprise at least one monoclonal antibody that specifically binds a light chain of the antibody of interest. In the context of bispecific antibodies, the primary antibody or antibodies may be directed against different heavy chains to identify species comprising unwanted homodimers and the desired heterodimeric species. In some embodiments, the one or more primary antibodies comprise at least one monoclonal antibody that specifically binds both a light chain and a heavy chain of the antibody of interest. In some embodiments, the one or more primary antibodies comprise at least one monoclonal antibody that specifically binds to one or more of the CDRs of the antibody of interest. In some embodiments, the sample includes one or more internal standards, for example a ladder of molecular weight standards, a ladder of isoelectric point standards, or even a standard used as a baseline or benchmark for determining the amount of a mAb of interest in the sample.

The ability to discriminate between mAbs in a mAb cocktail of multiple mAbs is becoming increasingly important as these multiple component therapies demonstrate increased efficacy in disease treatment. Thus, improved methods of monitoring how the individual mAbs behave in these systems will become increasingly important in the assessment of the compatibility and stability of these multi-mAb therapies. To meet this growing need this disclosure provides a method for detecting and/or discriminating between monoclonal antibodies in a mixture of two of more monoclonal antibodies in a sample.

Figure 12:
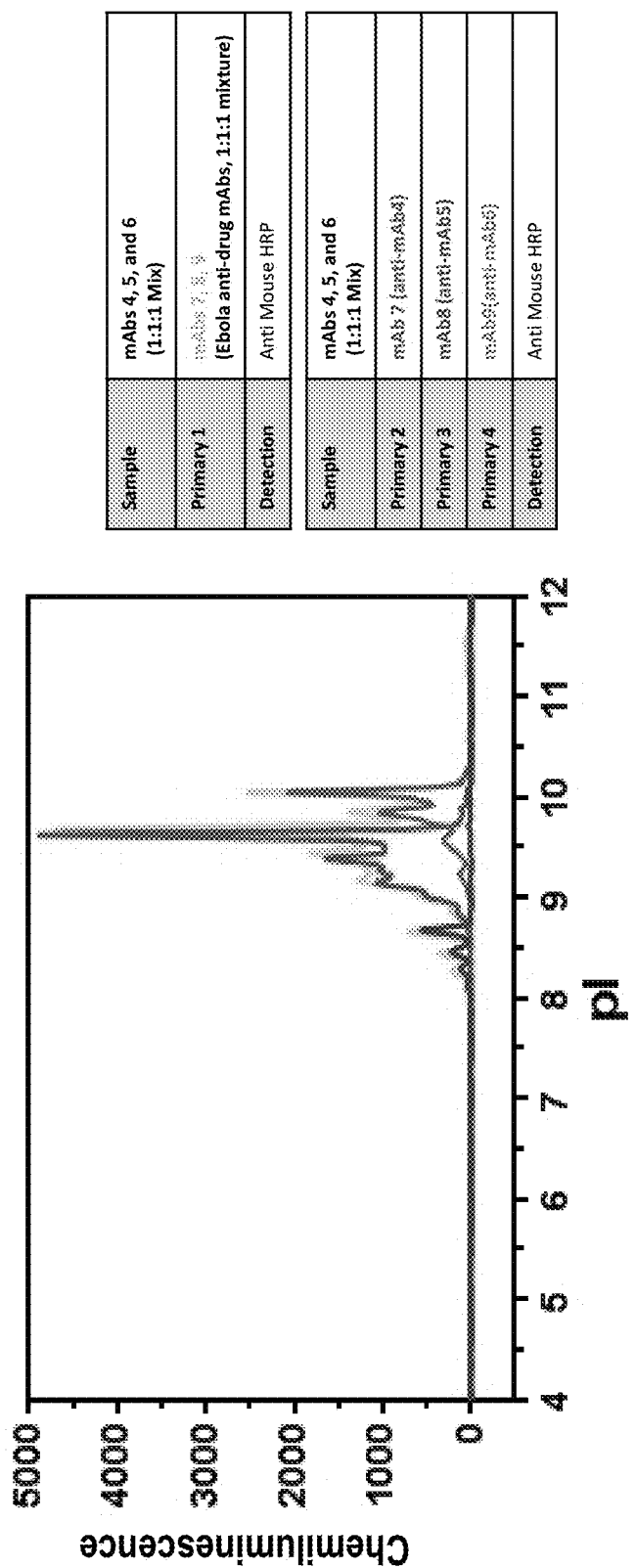
FIG. 12 is a composite graph showing that iCIEF-Western has the power to selectively detect the individual antibodies in a combination drug product.

In embodiments, the method includes separating protein components of a sample with two or more mAbs of interest, such as 2, 3, 4, 5, 6, 7, 8, 9 10 or even more, mAbs of interest, by charge in one or more capillaries using capillary electrophoresis, for example by isoelectric focusing. In embodiments, the method includes immobilizing the protein components of the sample within the one or more capillaries. In embodiments, the method includes contacting the protein components within the one or more capillaries with a first primary antibody that specifically binds to a first monoclonal antibody of interest. In embodiments, the method includes detecting the binding of the first primary antibody, thereby detecting the first monoclonal antibody of interest. In some embodiments, a charge based profile or fingerprint of the mAbs of interest can be created, for example of the mAb of interest alone for comparison with a charge based profile or fingerprint of the mAbs in the mixture. This comparison can then be used to determine if the mAb of interest changes in the mixture. This profile or fingerprint comparison can be done for any or all of the mAbs of interest in the mixture. In embodiments, the method includes contacting the protein components within the one or more capillaries with a second primary antibody that specifically binds to a second monoclonal antibody of interest. In embodiments, the method includes detecting the binding of the a second primary antibody, thereby detecting the second monoclonal antibody of interest and discriminating between the monoclonal antibodies in a sample. This can be continued for multiple different mAbs in the sample. For example, in embodiments, the method can include contacting the protein components within the one or more capillaries with a third primary antibody that specifically binds to a third monoclonal antibody of interest and detecting the binding of the third primary antibody, thereby detecting the third monoclonal antibody of interest. In additional embodiments, the method can include contacting the protein components within the one or more capillaries with a one or more additional primary antibodies, for example a $4^{th}$, $5^{th}$, $6^{th}$, $7^{th}$ and so on, primary antibody, that specifically binds to one or more additional monoclonal antibodies of interest, for example a $4^{th}$, $5^{th}$, $6^{th}$, $7^{th}$, and so on additional monoclonal antibody of interest, and detecting the binding of the one or more additional primary antibodies, thereby detecting the additional monoclonal antibodies of interest. In embodiments, the sample is spit into multiple capillaries and each of these capillaries are contacted with a different primary antibody or antibodies and detected. The signals obtained can be later combined, for example as shown in FIG. 12. In certain embodiments, the detection can take place in a single capillary, for example in multiplex as described below.

In addition to the characterization of mAbs as described above, understanding the nature of protein contaminants is another important factor in the development of mAb therapeutics. For example, control of residual protein A, HCP, residual DNA and other potential culture or purification residues are typically part of the drug substance specification. In addition, such control provides valuable information on process consistency and performance. Thus, disclosed herein are size and/or charge based detection methods for Host Cell Proteins (HCPs), for example using antibodies, such as monoclonal or polyclonal antibodies specific for the HCPs, e.g. contaminating proteins of interest. The disclosed methods allow for the detection and visualization of problematic HCPs and their various species in process samples. These methods allow for the ability to detect and show the various species of a given HCP impurity at low ppm levels. Thus, aspects of this disclosure further include a method for detecting protein contaminants of interest in a monoclonal antibody preparation sample. In embodiments, the method includes separating protein components of a sample by a physical parameter in one or more capillaries using capillary electrophoresis. In embodiments, the method includes immobilizing the protein components of the sample within the one or more capillaries. In embodiments, the method includes contacting the protein components within the one or more capillaries with one or more primary antibodies that specifically bind to a protein contaminant of interest. In embodiments, the method includes detecting the binding of the one or more primary antibodies, thereby detecting the protein contaminants of interest in a monoclonal antibody preparation sample. In some embodiments, the method further includes discriminating between variants of a protein contaminant of interest in a monoclonal antibody preparation sample by the physical parameter. In embodiments, the protein of interest is a contaminating protein of interest or more than one contaminating protein of interest, that can be detected with one or more primary antibodies, for example monoclonal antibodies or even polyclonal antibodies. In some embodiments, the method includes detecting and/or discriminating between charge or size variants of the protein contaminants of interest. In some embodiments, a relative or absolute amount of the protein contaminants of interest can be determined. In some embodiments, the protein contaminants of interest comprise PLBD2.

Samples for use in the disclosed methods can be heterogeneous, containing a variety of components, i.e. different proteins. Alternatively, the sample can be homogenous, containing one component or essentially one component of multiple charge or molecular weight species. Pre-analysis processing may be performed on the sample prior to detecting the protein of interest, such as a mAb or contaminating protein. For example, the sample can be subjected to a lysing step, denaturation step, heating step, purification step, precipitation step, immunoprecipitation step, column chromatography step, centrifugation, etc. In some embodiments, the separation of the sample and immobilization may be performed on native substrates. In other embodiments, the sample may be subjected to denaturation, for example, heat and/or contact with a denaturizing agent. Denaturizing agents are known in the art. In some embodiments, the sample may be subjected to non-reducing conditions. In some embodiments, the sample may be subjected to reducing conditions, for example contacted with one or more reducing agents. Reducing agents are knowns in the art.

In some embodiments, the primary antibodies are labeled with a detectable label and detecting the binding of the one or more primary antibodies comprises detecting the detectable label. In some embodiments, detecting the binding of the one or more primary antibodies includes contacting the one or more primary antibodies with a secondary antibody that specifically binds at least one of the one or more primary antibodies and detecting the binding of the secondary antibody. In embodiments, the secondary antibody has a detectable label and the detectable label is detected.

In some embodiments, the primary antibodies and/or secondary antibodies include one or more detectable labels. In some embodiments, the detectable label comprises a chemiluminescent label, a fluorescent label or bioluminescent label. In some embodiments, the detectable label includes a chemiluminescent label. The chemiluminescent label can include any entity that provides a light signal and that can be used in accordance with the methods disclosed herein. A variety of such chemiluminescent labels are known in the art, see for example, e.g., U.S. Pat. Nos. 6,689,576, 6,395,503, 6,087,188, 6,287,767, 6,165,800, and 6,126,870, which are incorporated herein by reference in its entirety. Suitable labels include enzymes capable of reacting with a chemiluminescent substrate in such a way that photon emission by chemiluminescence is induced. Such enzymes induce chemiluminescence in other molecules through enzymatic activity. Such enzymes may include peroxidase, such as horse radish peroxidase (HRP), beta-galactosidase, phosphatase, or others for which a chemiluminescent substrate is available. In some embodiments, the chemiluminescent label can be selected from any of a variety of classes of luminol label, an isoluminol label, etc. In some embodiments, the primary antibodies include chemiluminescent labeled antibodies. Chemiluminescent substrates are well known in the art, such as Galacton substrate available from Applied Biosystems of Foster City, Calif. or SuperSignal West Femto Maximum Sensitivity substrate available from Pierce Biotechnology, Inc. of Rockford, Ill. or other suitable substrates.

In some embodiments, the detectable label includes a bioluminescent compound. Bioluminescence is a type of chemiluminescence found in biological systems in which a catalytic protein increases the efficiency of the chemiluminescent reaction. The presence of a bioluminescent compound is determined by detecting the presence of luminescence. Suitable bioluminescent compounds include, but are not limited to luciferin, luciferase and aequorin.

In some embodiments, the detectable label includes a fluorescent label, such as a fluorescent dye. A fluorescent dye can include any entity that provides a fluorescent signal and that can be used in accordance with the methods and devices described herein. Typically, the fluorescent dye includes a resonance-delocalized system or aromatic ring system that absorbs light at a first wavelength and emits fluorescent light at a second wavelength in response to the absorption event. A wide variety of such fluorescent dye molecules are known in the art. For example, fluorescent dyes can be selected from any of a variety of classes of fluorescent compounds, non-limiting examples include xanthenes, rhodamines, fluoresceins, cyanines, phthalocyanines, squaraines, bodipy dyes, coumarins, oxazines, and carbopyronines. In some embodiments, for example, where primary and/or secondary antibodies contain fluorophores, such as fluorescent dyes, their fluorescence is detected by exciting them with an appropriate light source, and monitoring their fluorescence by a detector sensitive to their characteristic fluorescence emission wavelength. In some embodiments, the primary antibodies include fluorescent dye labeled antibodies.

In embodiments, using two or more different primary or secondary antibodies, which bind to or interact with different protein of interests, such as different mAbs or contaminant proteins of interest, different types of proteins of interests can be detected simultaneously, for example in multiplex within the same or a single capillary, for example using different or even the same detectable label. In some embodiments, two or more different primary and/or second antibodies, which bind to or interact with the one protein of interest, can be detected simultaneously. By way of non-limiting example, a first primary antibody that binds a heavy chain of a mAb of interest having a first detectable label can be detected with a second primary antibody that binds a light chain of a mAb of interest having a second detectable label differing from the first detectable label, such that the two labels can be detected in multiplex. In some embodiments, multiple primary and/or secondary antibodies can be used with multiple substrates to provide color-multiplexing. For example, the different chemiluminescent substrates used would be selected such that they emit photons of differing color. Selective detection of different colors can be accomplished by using a diffraction grating, prism, series of colored filters, or other means.

In embodiments, the capillary may include a separation matrix, which can be added in an automated fashion by the apparatus and/or system. In some embodiments, the sample is loaded onto a stacker matrix prior to separation. The separation matrix, in one embodiment, is a size separation matrix, and has similar or substantially the same properties of a polymeric gel, used in conventional electrophoresis techniques. Capillary electrophoresis in the separation matrix is analogous to separation in a polymeric gel, such as a polyacrylamide gel or an agarose gel, where molecules are separated on the basis of the size of the molecules in the sample, by providing a porous passageway through which the molecules can travel. The separation matrix permits the separation of molecules by molecular size because larger molecules will travel more slowly through the matrix than smaller molecules. In some embodiments, the one or more capillaries comprise a separation matrix. In some embodiments, the sample containing a protein of interest is separated or resolved based on molecular weight. In some embodiments, the separation matrix comprises a sieving matrix configured to separate proteins by molecular weight. In some embodiments, protein components of a sample are separated by molecular weight and the method is a method of detecting and/or discriminating between size variants of monoclonal antibody of interest. In some embodiments, protein components of a sample are separated by molecular weight and the method is a method of detecting and/or discriminating between size variants of a contaminating protein of interest.

A wide variety of solid phase substrates are known in the art, for example gels, such as polyacrylamide gel. In some embodiments, resolving one or more proteins of interest includes electrophoresis of a sample in a polymeric gel. Electrophoresis in a polymeric gel, such as a polyacrylamide gel or an agarose gel separates molecules on the basis of the molecule's size. A polymeric gel provides a porous passageway through which the molecules can travel. Polymeric gels permit the separation of molecules by molecular size because larger molecules will travel more slowly through the gel than smaller molecules.

In some embodiments, the sample containing a protein of interest is separated or resolved based on the charge of the components of the sample. In some embodiments, protein components of a sample are separated by charge and the method is a method of detecting and/or discriminating between charge variants of a monoclonal antibody of interest. In some embodiments, protein components of a sample are separated by charge and the method is a method of detecting and/or discriminating between charge variants of a contaminating protein of interest. In some embodiments, the separation matrix comprises carrier ampholytes. In some embodiments, separating a sample by charge includes isoelectric focusing (IEF) of a sample. For example, in an electric field, a molecule will migrate towards the pole (cathode or anode) that carries a charge opposite to the net charge carried by the molecule. This net charge depends in part on the pH of the medium in which the molecule is migrating. One common electrophoretic procedure is to establish solutions having different pH values at each end of an electric field, with a gradient range of pH in between. At a certain pH, the isoelectric point of a molecule is obtained and the molecule carries no net charge. As the molecule crosses the pH gradient, it reaches a spot where its net charge is zero (i.e., its isoelectric point) and it is thereafter immobilized in the electric field. Thus, this electrophoresis procedure separates molecules according to their different isoelectric points.

In some embodiments, for example, when resolving is by isoelectric focusing, an ampholyte reagent can be loaded into one or more capillaries of a capillary electrophoresis device. An ampholyte reagent is a mixture of molecules having a range of different isoelectric points. Typical ampholyte reagents are Pharmalyte™ and Ampholine™ available from Amersham Biosciences of Buckinghamshire, England.

In embodiments, once the separation is complete, the components of the separated sample (e.g., including the protein of interests, such as a mAb or contaminating protein of interest) are immobilized to a wall(s) of the one or more capillaries using any suitable method including but not limited to chemical, photochemical, and heat treatment. In some embodiments, the components of the separated sample are immobilized in one or more capillaries of a CE-system after the molecules have been separated by electrophoresis, for example by size or charge. In some embodiments, the immobilizing comprises photo-immobilizing, chemically immobilizing, or thermally immobilizing. The immobilization can be via covalent bonds or non-covalent means such as by hydrophobic or ionic interaction. In certain embodiments the protein(s) of interest are immobilized using one or more reactive moieties. The reactive moiety can include any reactive group that is capable of forming a covalent linkage with a corresponding reactive group of individual molecules of the sample. Thus, the reactive moiety can include any reactive group known in the art, so long as it is compatible with the methods disclosed herein. In some embodiments, the reactive moiety includes a reactive group that is capable of forming a covalent linkage with a corresponding reactive group of an protein of interest, such as a mAb or contaminating protein of interest.

The reactive moiety can be attached directly, or indirectly to the capillary. In some embodiments, the reactive moiety can be supplied in solution or suspension, and may form bridges between the wall of the capillary and the molecules in the sample upon activation. For example, in one embodiment, immobilization occurs by subjecting the separated sample and the capillaries to ultraviolet (UV) light, which serves to immobilize the protein of interest(s) (if present in the sample) and molecules in the sample to the walls of the capillary. The immobilization can be via covalent bonds or non-covalent means such as by hydrophobic or ionic interaction. In another embodiment, a reactive moiety can be used to covalently immobilize the resolved protein of interest or proteins of interest in the capillary. The reactive moiety can be attached directly or indirectly to the capillary (e.g., on the wall(s) of the capillary tube). In some embodiments, the reactive moiety can be supplied in solution or suspension, and can be configured to form bridges between the wall of the capillary and the molecules in the sample upon activation. The reactive moiety can line the capillary or can be present on a linear or cross-linked polymer in the capillary, which may or may not be linked to the wall of the capillary before and/or after activation. The reactive moiety can be and/or can include any reactive group that is capable of forming a covalent linkage with a corresponding reactive group of individual molecules of the sample such as, for example, those described above.

In some embodiments, the reactive moiety includes a functional group that can be converted to a functionality that adheres to a protein of interest via hydrophobic interactions, ionic interactions, hydrogen bonding etc. In some embodiments, such reactive moieties are activated with UV light, a laser, temperature, or any other source of energy in order to immobilize the protein of interest onto the surfaces of the capillary and/or onto the surfaces of particles attached to the surfaces of the capillary. In some embodiments, the surfaces of the capillary are functionalized with thermally responsive polymers that enable changes in hydrophobicity of the surfaces upon changing the temperature. In some embodiments, the proteins of interest are immobilized on such surfaces by increasing hydrophobicity of a temperature responding polymer when a certain temperature is reached within the capillary.

A wide variety of reactive moieties suitable for covalently linking two molecules together are known in the art. For example, the reactive moiety can bind to carbon-hydrogen (C—H) bonds of proteins. Since many separation media also contain components with C—H bonds, chemistries that react with sulfhydryl (S—H) groups may be advantageous in that S—H groups are found uniquely on proteins relative to most separation media components. Suitable reactive moieties include, but are not limited to, photoreactive groups, chemical reactive groups, and thermoreactive groups. Photoimmobilization in the capillary system can be accomplished by the activation of one or more photoreactive groups. A photoreactive group includes one or more latent photoreactive groups that upon activation by an external energy source, forms a covalent bond with other molecules. See, e.g., U.S. Pat. Nos. 5,002,582 and 6,254,634. The photoreactive groups generate active species such as free radicals and particularly nitrenes, carbenes, and excited states of ketones upon absorption of electromagnetic energy. The photoreactive groups can be chosen that are responsive to various portions of the electromagnetic spectrum, such as those responsive to ultraviolet, infrared and visible portions of the spectrum. For example, upon exposure to a light source, the photoreactive group can be activated to form a covalent bond with an adjacent molecule. Suitable photoreactive groups include, but are not limited to, aryl ketones, azides, diazos, diazirines, and quinones. In some embodiments, the resolved proteins of interest of the sample are immobilized in the capillary of a CE-system by isoelectric focusing.

Detecting a detectable label can be by any method known in the art, so long as it is compatible with the methods described herein. Label detection can be performed by monitoring a signal using conventional methods and instruments, non-limiting examples include, a photodetector, an array of photodetectors, a charged coupled device (CCD) array, etc. Typically, detecting the detectable label includes imaging the capillary. In some embodiments, the entire length of the capillary can be imaged. Alternatively, a distinct part or portion of the capillary can be imaged.

Variations of order of the steps of the methods described herein will readily occur to those skilled in the art. For example, the sample can be separated and then the protein of interest(s) immobilized at their resolved locations in the capillary, prior to contacting the protein of interest(s) with the primary antibodies. In some embodiments, primary antibodies are contacted with the protein of interest(s) to form a complex and then the complex is resolved in the capillary of a CE-system. In some embodiments, the primary antibodies could be preloaded into the sample and thereafter loaded into the system. As another example, the resolving step, such as isoelectric focusing, can be applied after the chemiluminescent reagents are supplied.

In some embodiments, sample includes an internal standard. Internal standards serve to calibrate the separation with respect to isoelectric point or molecular weight. Internal standards for IEF are well known in the art, for example see, Shimura, K., Kamiya, K., Matsumoto, H., and K. Kasai (2002) Fluorescence-Labeled Peptide pI Markers for Capillary Isoelectric Focusing, Analytical Chemistry v74: 1046-1053, and U.S. Pat. No. 5,866,683. Standards to be detected by fluorescence could be illuminated either before or after chemiluminescence, but generally not at the same time as chemiluminescence. In some embodiments, the protein of interest and standards are detected by fluorescence. The protein of interest and standards can each be labeled with fluorescent dyes that are each detectable at discrete emission wavelengths, such that the protein of interest and standards are independently detectable.

In some embodiments, an internal standard can be a purified form of the protein of interest itself, which is generally made distinguishable from the protein of interest in some way. Methods of obtaining a purified form of the protein of interest can include, but are not limited to, purification from nature, purification from organisms grown in the laboratory (e.g., via chemical synthesis), and/or the like. The distinguishing characteristic of an internal standard can be any suitable change that can include, but is not limited to, dye labeling, radiolabeling, or modifying the mobility of the standard during the electrophoretic separation so that it is separated from the protein of interest. For example, a standard can contain a modification of the protein of interest that changes the charge, mass, and/or length (e.g., via deletion, fusion, and/or chemical modification) of the standard relative to the protein of interest. Thus, the protein of interest and the internal standard can each be labeled with fluorescent dyes that are each detectable at discrete emission wavelengths, thereby allowing the protein of interest and the standard to be independently detectable. In some instances, an internal standard is different from the protein of interest but behaves in a way similar to or the same as the protein of interest, enabling relevant comparative measurements. In some embodiments, a standard that is suitable for use can be any of those described in U.S. Patent Application Publication No. 2007/0062813, the disclosure of which is incorporated herein by reference in its entirety.

As will be appreciated by those in the art, virtually any method of loading the sample in the capillary may be performed. For example, the sample can be loaded into one end of the capillary. In some embodiments, the sample is loaded into one end of the capillary by hydrodynamic flow. For example, in embodiments wherein the fluid path is a capillary, the sample can be loaded into one end of the capillary by hydrodynamic flow, such that the capillary is used as a micropipette. In some embodiments, the sample can be loaded into the capillary by electrophoresis, for example, when the capillary is gel filled and therefore more resistant to hydrodynamic flow.

The capillary can include any structure that allows liquid or dissolved molecules to flow. Thus, the capillary can include any structure known in the art, so long as it is compatible with the methods. In some embodiments, the capillary is a bore or channel through which a liquid or dissolved molecule can flow. In some embodiments, the capillary is a passage in a permeable material in which liquids or dissolved molecules can flow.

The capillary includes any material that allows the detection of the protein of interest within the capillary. The capillary includes any convenient material, such as glass, plastic, silicon, fused silica, gel, or the like. In some embodiments, the method employs a plurality of capillaries. A plurality of capillaries enables multiple samples to be analyzed simultaneously.

The capillary can vary as to dimensions, width, depth and cross-section, as well as shape, being rounded, trapezoidal, rectangular, etc., for example. The capillary can be straight, rounded, serpentine, or the like. As described below, the length of the fluid path depends in part on factors such as sample size and the extent of sample separation required to resolve the protein of interest.

In some embodiments, the capillary includes a tube with a bore. In some embodiments, the method employs a plurality of capillaries. Suitable sizes include, but are not limited to, capillaries having internal diameters of about 10 to about 1000 μm, although more typically capillaries having internal diameters of about 25 to about 400 μm can be utilized. Smaller diameter capillaries use relatively low sample loads while the use of relatively large bore capillaries allows relatively high sample loads and can result in improved signal detection.

The capillaries can have varying lengths. Suitable lengths include, but are not limited to, capillaries of about 2 to 20 cm in length, although somewhat shorter and longer capillaries can be used. In some embodiments, the capillary is about 3, 4, 5, or 6 cms in length. Longer capillaries typically result in better separations and improved resolution of complex mixtures. Longer capillaries can be of particular use in resolving low abundance proteins of interest.

Generally, the capillaries are composed of fused silica, although plastic capillaries and PYREX (i.e., amorphous glass) can be utilized. As noted above, the capillaries do not need to have a round or tubular shape. Other shapes, so long as it is compatible with the methods described herein, may also be used.

In some embodiments, the capillary can be a channel. In some embodiments, the method employs a plurality of channels. In some embodiments, the capillary can be a channel in a microfluidic device. Microfluidics employs channels in a substrate to perform a wide variety of operations. The microfluidic devices can include one or a plurality of channels contoured into a surface of a substrate. The microfluidic device can be obtained from a solid inert substrate, and in some embodiments in the form of a chip. The dimensions of the microfluidic device are not critical, but in some embodiments the dimensions are on the order of about 100 μm to about 5 mm thick and approximately about 1 centimeter to about 20 centimeters on a side. Suitable sizes include, but are not limited to, channels having a depth of about 5 μm to about 200 μm, although more typically having a depth of about 20 μm to about 50 μm can be utilized. Smaller channels, such as micro or nanochannels can also be used, so long as they are compatible with the methods.

Although specific embodiments have been described above in detail, the description is merely for purposes of illustration. It should be appreciated, therefore, that many aspects described above are not intended as required or essential elements unless explicitly stated otherwise. Modifications of, and equivalent components or acts corresponding to, the disclosed aspects of the example embodiments, in addition to those described above, can be made by a person of ordinary skill in the art, having the benefit of the present disclosure, without departing from the spirit and scope of embodiments defined in the following claims, the scope of which is to be accorded the broadest interpretation so as to encompass such modifications and equivalent structures.

The following examples are provided to illustrate particular features of certain embodiments. However, the particular features described below should not be considered as limitations on the scope of the invention, but rather as examples from which equivalents will be recognized by those of ordinary skill in the art.

EXAMPLES

Example 1

Quantitation of Size Variants in mAb Samples by CE-Western

Figure 3A:
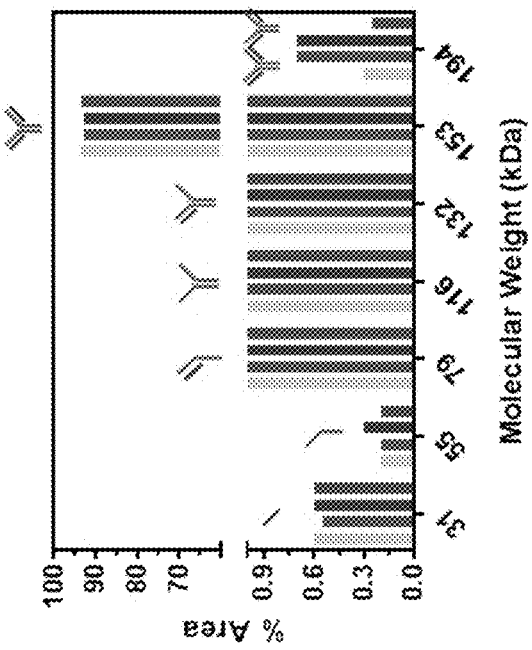
FIG. 3A is a bar graph of the relative amount of the antibody fragments as shown in FIG. 2A.
Figure 3B:
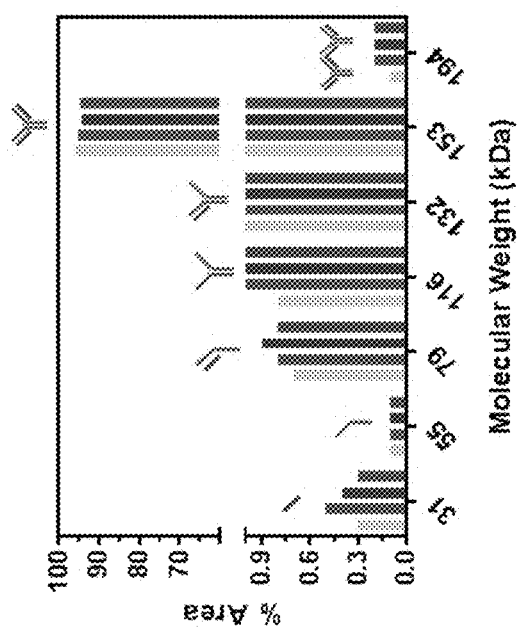
FIG. 3B is a bar graph of the relative amount of the antibody fragments as shown in FIG. 2B.

Samples containing a purified antibody preparation of mAb1 were subjected to CE separation by molecular weight (see FIG. 1) using a PeggySue device as obtained from ProteinSimple, San Jose, Calif. The resulting separations were analyzed either by using anti-Kappa and anti-FC antibodies (FIG. 2A) or by total protein assay (see below). As shown in FIG. 2A, using the antibodies for the light and heavy chains of mAb1 allowed for the identification of the size variants in the sample according to molecular weight, as well as a determination of the relative amount of each of the size variants. As shown in FIG. 2B, the results as shown in FIG. 2A were the same as those obtained in a total protein assay, i.e. where the fluorescent signal from any protein in the sample is determined. FIG. 2B in combination with FIG. 2A demonstrates that the size variants can be quantitated using antibody detection and any bias in the antibody based detection can be confirmed using the total protein assay. Furthermore, this result demonstrates that size based CE-western can sensitively quantitate size variants in mAb samples. FIGS. 3A and 3B show the relative amounts of the detected antibodies or fragments thereof.

Size Assay

Reconstitution of the standard fluorescent mix, DTT, ladder and luminol was performed according to the manufacturer's instructions. The standard sample preparation condition is to heat the samples at 95 t for 5 minutes. For the resolution needed, the samples were heated at 80° C. for 10 minutes. Further, the instrument parameters were optimized to improve the resolution by changing the stacking and sample loading time. While the manufacturer recommends using a 15-sec stacking matrix followed by a 9-sec sample loading time, the current standard condition is a 12-sec stacking matrix followed by a 6-sec sample loading time which significantly improved the resolution between the 150 kDa and the 125 kDa peak in the antibody size variant characterization.

Total Protein Assay:

In the optimized methods disclosed herein, online biotinylation of the samples on the size assay module was performed without having to use the total protein assay module. This gave provided the capability to run the total protein assay in parallel to the size assay within the same cycle which isn't possible otherwise.

As a second approach, pre-biotinylated samples were used in place of the online biotinylation to improve the method sensitivity. In addition to improving the sensitivity, it allows us to run the total protein assay in parallel to the size assay within the same cycle by eliminating the use of total protein kit and the module.

Example 2

Comparison of CE-Western and CE-SDS

Figure 4:
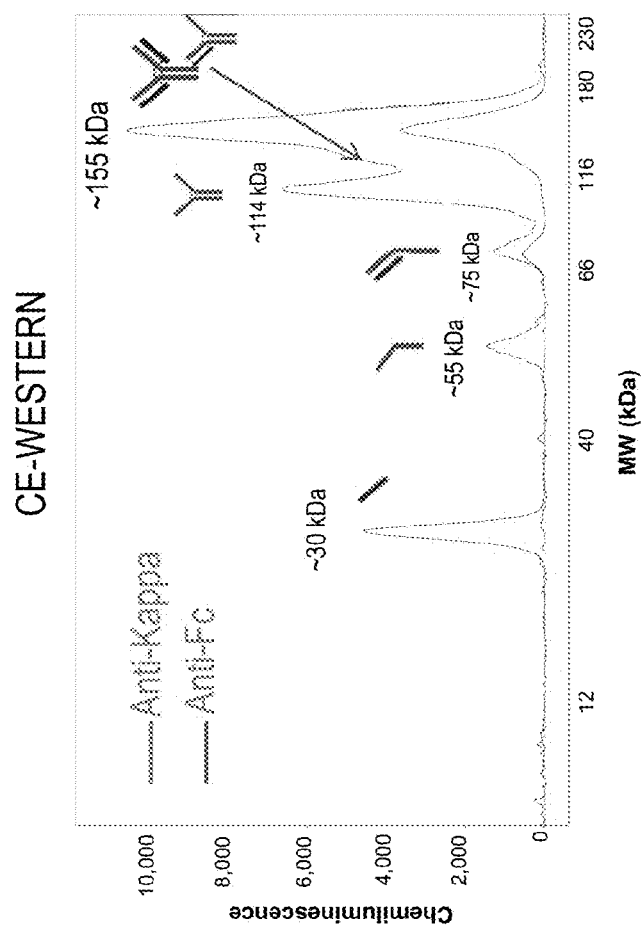
FIG. 4 shows two graphs demonstrating that the analysis of antibody fragments using size based CE-Western is comparable to the analysis of antibody fragments using CE-SDS.
Figure 4:
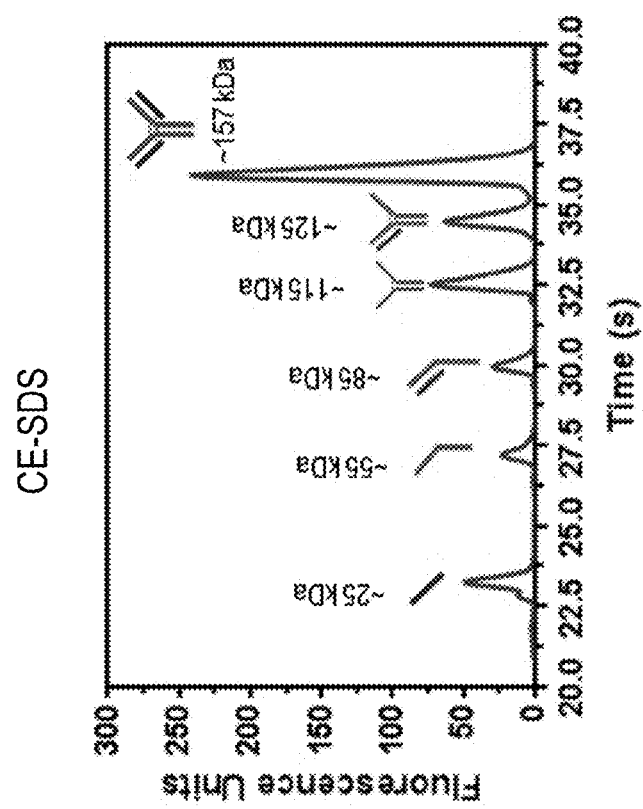

Samples containing mAb1 were subjected to either CE-SDS analysis or size based CE-Western analysis. As shown in FIG. 4, the size based CE-Western analysis provided comparable resolution to the CE-SDS analysis. In addition, because the size based CE-Western analysis used two different antibodies, it is possible to determine which size variant gives rise to which peak in the analysis (the right panel is a composite of two traces, one where the resolved sample was probed with an anti-Kappa antibody or an anti-FC antibody). These results demonstrate that size based CE Western is a viable alternative to CE-SDS in the analysis of mAb size variants.

Example 3

Determination of Sample Contaminants in mAb Preparations

Figure 5A:
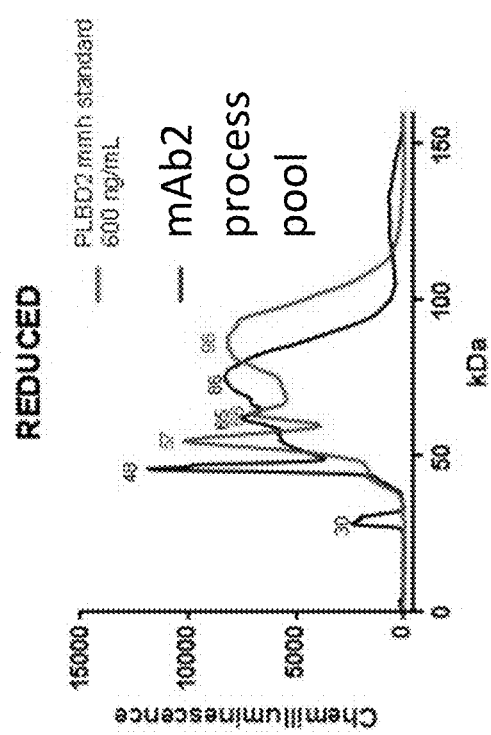
FIG. 5A is a graph of the analysis under non-reducing conditions showing that the exemplary mAb2 process pool has very similar PLBD2 species as in recombinant PLBD2.
Figure 5B:
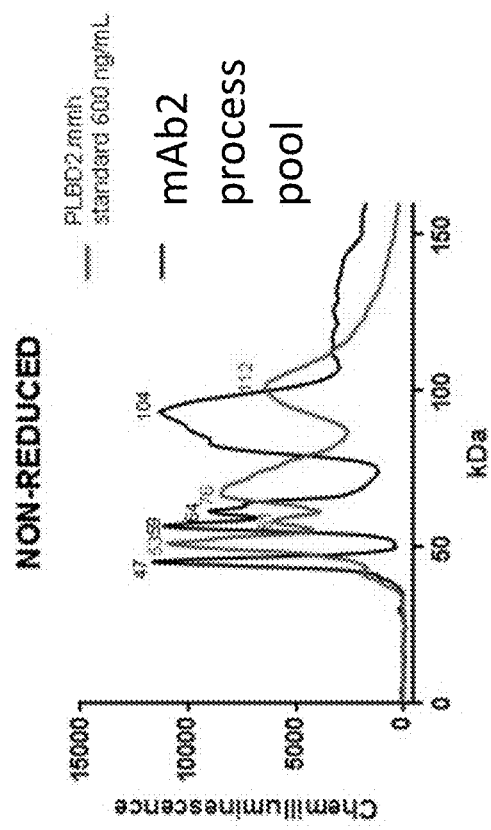
FIG. 5B is a graph of the analysis under reducing conditions showing that the exemplary mAb2 process pool has very similar PLBD2 species as in recombinant PLBD2.
Figure 6:
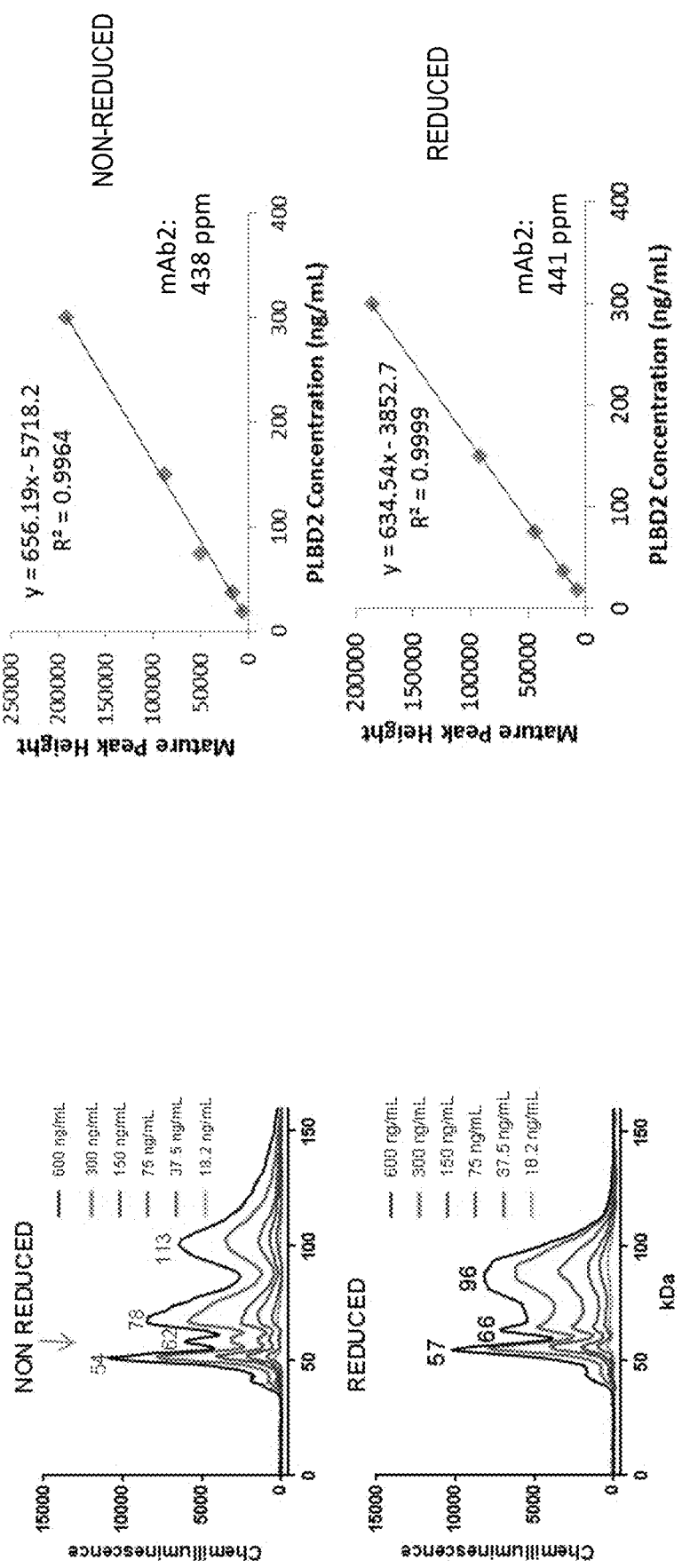
FIG. 6 shows a set of graphs demonstrating a concentration dependent analysis of PLBD2 in reducing and non-reducing conditions. This result shows that the quantitation of PLBD2 in antibody preparation samples by size based CE-western is comparable to ELISA measurement.

An antibody preparation that included the contaminant PLBD2 was analyzed by size based CE-Western under both non-reducing (FIG. 5A) and reducing (FIG. 5B) conditions. FIG. 5A is graph of the analysis under non-reducing conditions showing that the mAb2 process pool has very similar PLBD2 species as in recombinant PLBD2. FIG. 5B is graph of the analysis under reducing conditions showing that the mAb2 process pool has very similar PLBD2 species as in recombinant PLBD2. FIG. 6 is a set of graphs showing a concentration dependent analysis of PLBD2 in reducing and non-reducing conditions, which demonstrates that the size based CE-western is comparable to an ELISA measurement for the detection and quantification of mAb preparation contaminants. In addition, unlike ELISA, because the contaminating proteins can be resolved by molecular weight, the individual species contributing to the overall contamination can be determined.

Example 4

Separation and Detection on with Charge Based CE-Western

Figure 7:
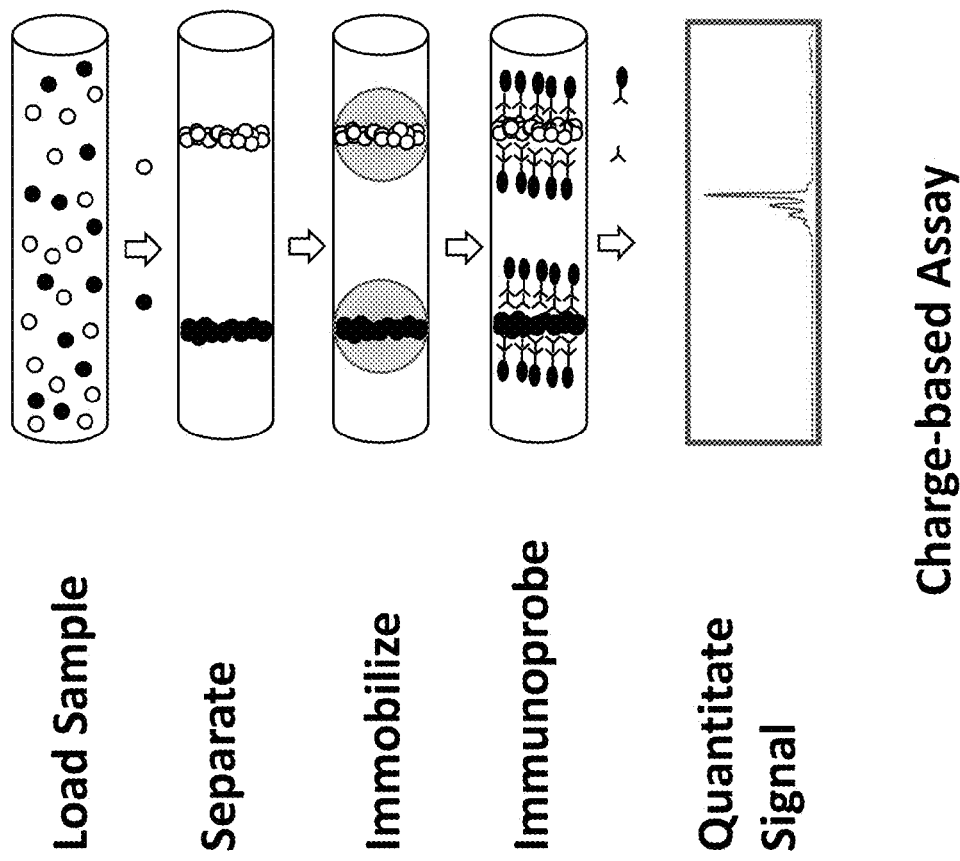
FIG. 7 is a diagram of an exemplary work flow for the separation and detection of proteins by capillary electrophoresis by charge.
Figure 8:
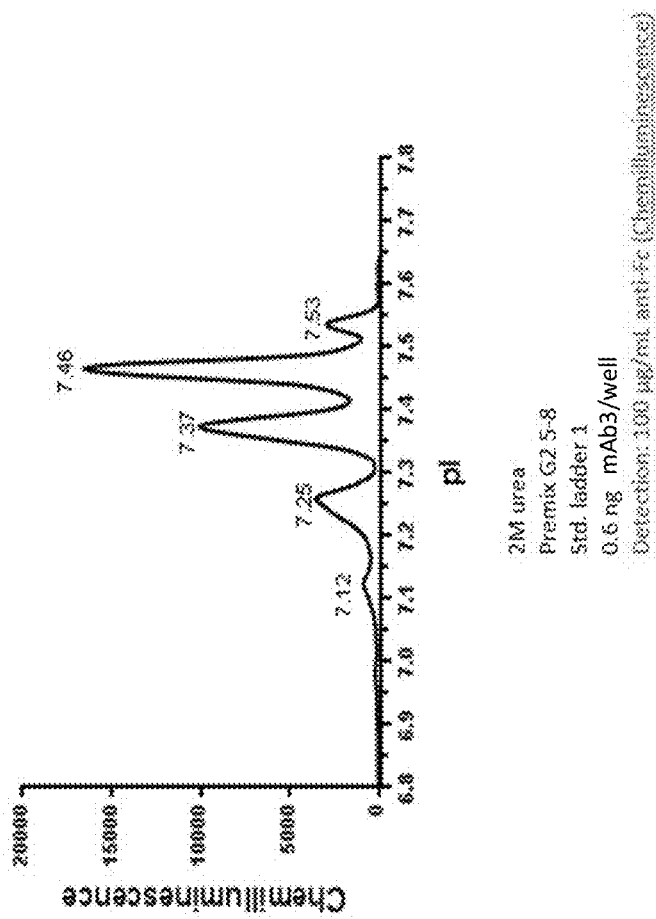
FIG. 8 shows that the results of imaged CIEF (iCIEF) and CE-Western are comparable for an antibody preparation. Comparable charge variant profiles were obtained by both iCIEF and iCIEF-Western. This result demonstrates that iCIEF-Western is a viable replacement for iCIEF for the analysis of antibodies.
Figure 8:
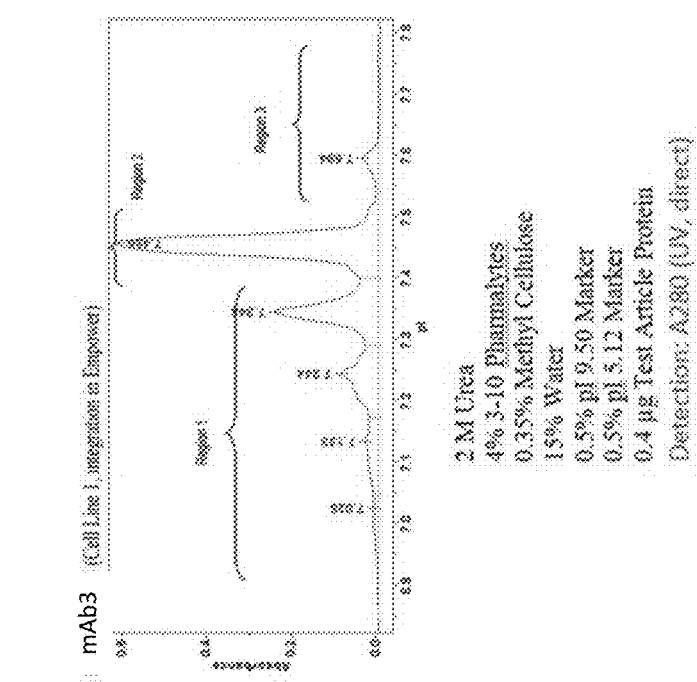
Figure 9B:
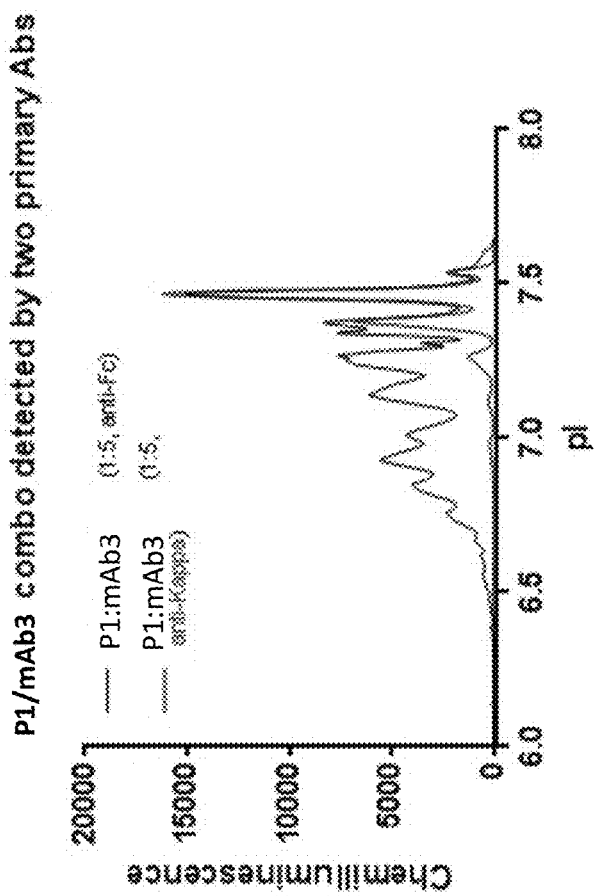
FIG. 9B is similar to the graph in FIG. 9A, but with the composite curve removed to show the individual antibody species.
Figure 9A:
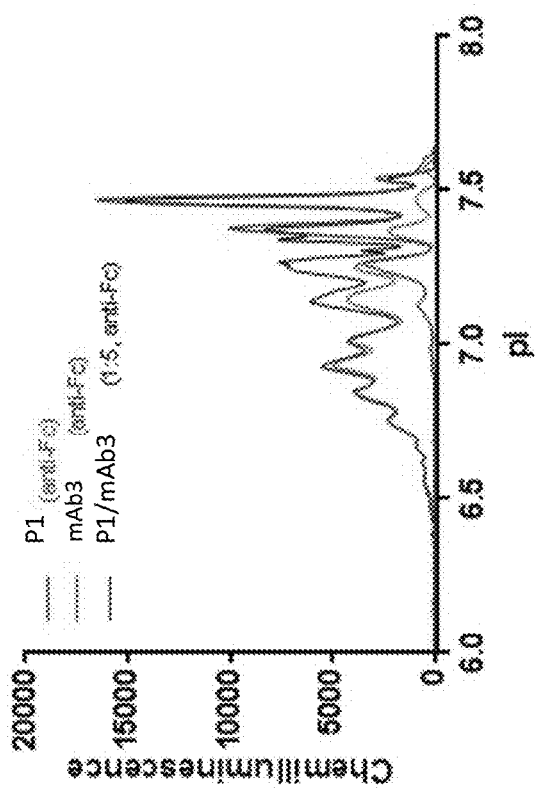
FIG. 9A is a graph showing charged based CE-western (iCIEF-western) is capable of determining the relative concentration of individual antibody species in a sample with secondary antibodies directed to the individual antibodies.

To demonstrate that charge based CE-Western (iCIEF-Western; see FIG. 7) was comparable to iCIEF in resolving mAb charge variants, samples including mAb3 were subjected to iCIEF and iCIEF-Western analysis. As shown in FIG. 8, iCIEF and iCIEF-Western gave comparable results for an antibody preparation. This result demonstrates that iCIEF-Western is a viable replacement for iCIEF for the analysis of antibodies. In addition, as shown in FIGS. 9A and 9B, because iCIEF-Western can use antibodies directed to the specific variants, the levels and identity of the variants can be determined simultaneously.

Charge Assay

Reconstitution of the premix G2, DTT and ladder was performed as suggested by the manufacturer's. According to the standard protocol, the sample dilution is recommended to perform in the sample diluent and DMSO inhibitor mixture. However, in the optimized method disclosed herein, the sample is diluted in the CHAPS/lysis buffer before adding to the premix G2 and pI ladder mix. In addition, TEMED was included as an additive in the sample preparation when working with molecules with high basic pI to bring the charge variant profile within the detection window. The sensitivity of the method was further improved by using size luminol in place of charge luminol as required.

The optimized method was used to detect and quantitate individual drugs within the combination products. Further, the method was used to understand the differences in the charge variants binding to the ligand.

Example 5

Analysis of Complex mAb Mixtures

Figure 10:
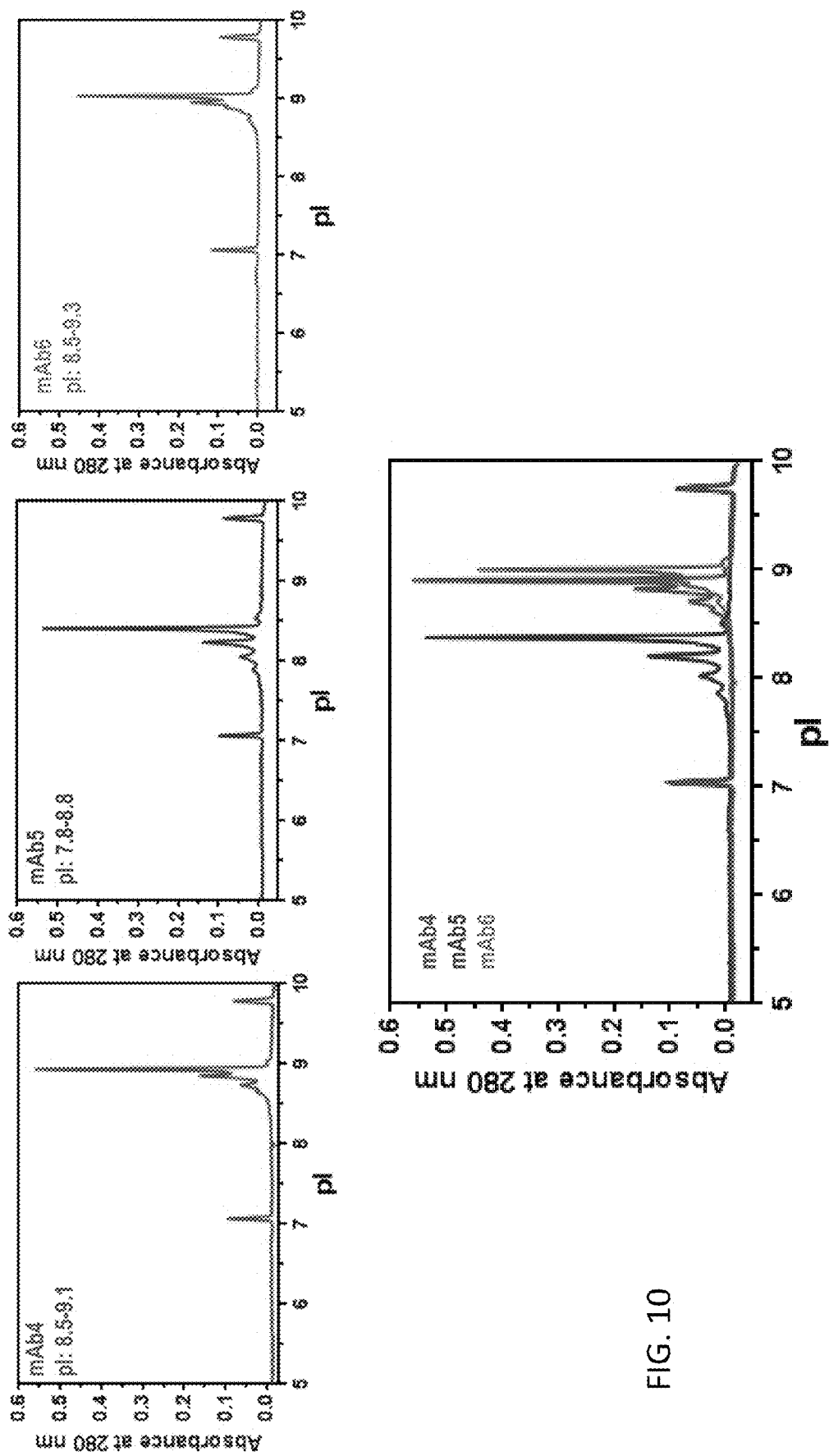
FIG. 10 shows a set of graphs illustrating the analysis of a three component antibody drug cocktail using iCIEF showing that the pI ranges of individual antibody charge variants are overlapping. This result demonstrates that iCIEF is ill equipped for the analysis of complex antibody preparations that are likely to have overlapping pIs.
Figure 11:
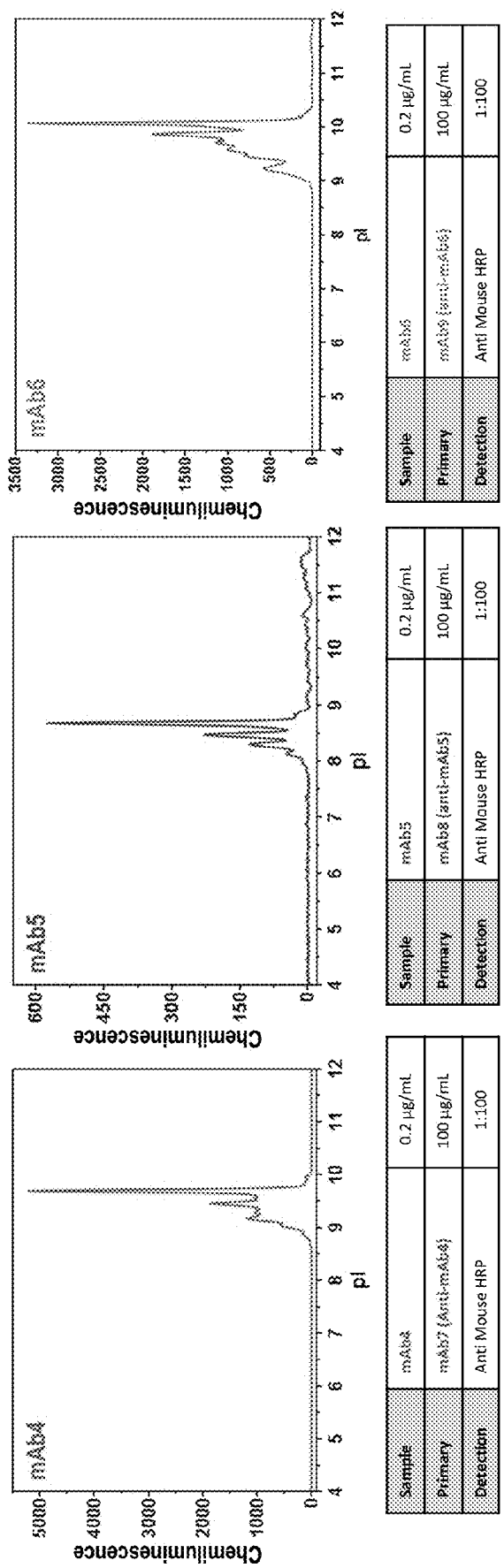
FIG. 11 shows a set of graphs and tables for the analysis of the individual species of the three component antibody drug cocktail from FIG. 10 as analyzed using charged based CE-Western (iCIEF-Western) and using secondary antibodies directed to the individual antibodies in the cocktail. TEMED (0.25%) was added to move the three antibody charge variants into the detection window of the capillary. This result demonstrates that iCIEF-western can be used to analyze complex antibody cocktails.
Figure 13:
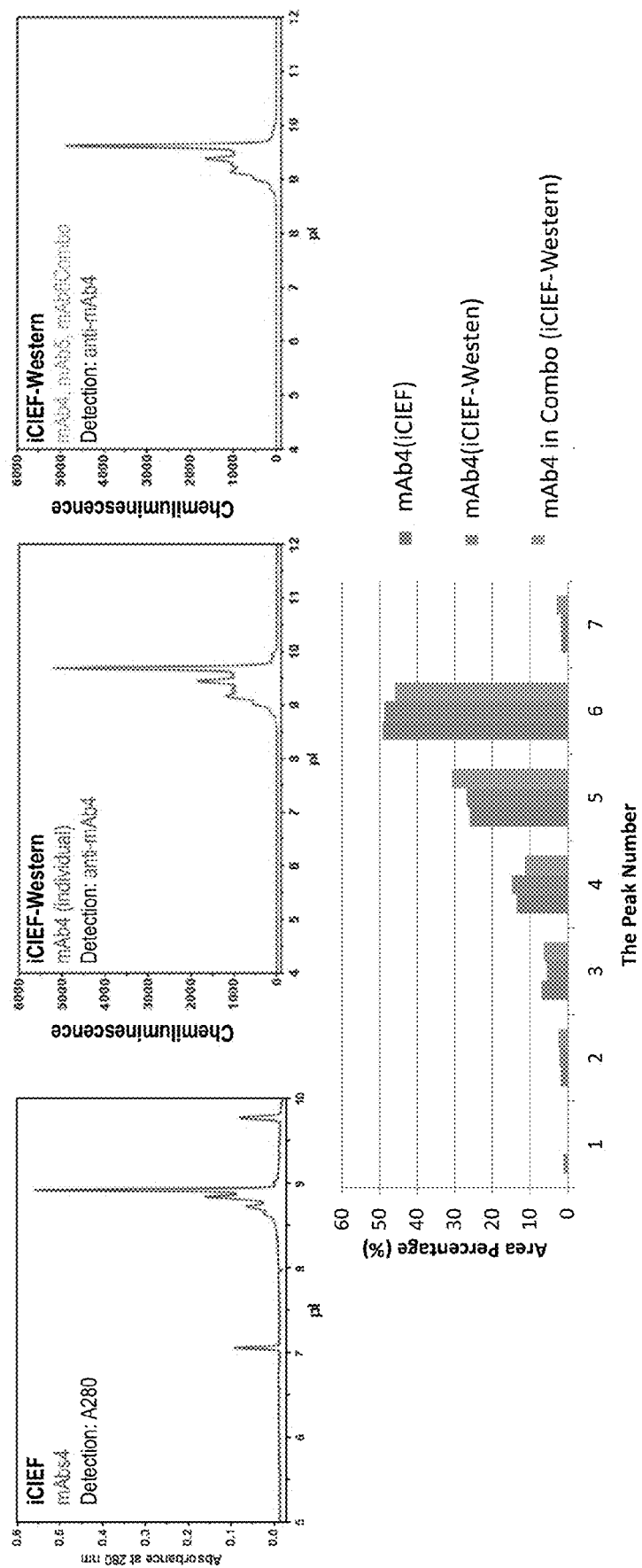
FIG. 13 shows graphs and a table demonstrating that the quantitative analysis of mAb4 is similar by itself as evaluated using iCIEF AND iCIEF-Western and in the combination as evaluated using iCIEF-Western.

The iCIEF-Western methods disclosed herein provide a powerful tool to analyze a complex antibody mixture. FIG. 10 shows that a three component antibody drug cocktail analyzed using iCIEF contains overlapping pI ranges of individual antibody charge variants. This result demonstrates that iCIEF is ill equipped for the analysis of complex antibody preparations that are likely to have overlapping pIs. However, as shown in FIG. 11, charged based CE-Western (iCIEF-Western) can be harnessed to discriminate between the individual species of the three component antibody drug cocktail. FIG. 12 illustrates a composite graph showing that iCIEF-Western has the power to selectively detect the individual antibodies in the combination drug product. As is shown in FIG. 13, quantitative analysis of mAb4 is similar by itself as evaluated using iCIEF and iCIEF-Western, and in the combination as evaluated using iCIEF-Western.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method for detecting and/or discriminating between variants of an antibody in a sample by a physical parameter, comprising:
    separating protein components of the sample comprising an antibody of interest by molecular weight or charge in one or more capillaries using capillary electrophoresis;
    immobilizing the protein components of the sample within the one or more capillaries;
    contacting the protein components within the one or more capillaries with two or more different primary antibodies that specifically bind to the antibody of interest; and
    detecting the binding of the two or more different primary antibodies, thereby detecting and/or discriminating between size variants or charge variants of the antibody of interest in the sample.

2. The method of claim 1, wherein the two or more different primary antibodies comprise at least one antibody that specifically binds a heavy chain of the antibody of interest.

3. The method of claim 1, wherein the two or more different primary antibodies comprise at least one antibody that specifically binds a light chain of the antibody of interest.

4. The method of claim 1, wherein the two or more different primary antibodies are labeled with a detectable label, and wherein detecting the binding of the two or more different primary antibodies comprises detecting the detectable label.

5. The method of claim 1, wherein detecting the binding of the two or more different primary antibodies comprises:
    contacting the two or more different primary antibodies with a secondary antibody that specifically binds at least one of the two or more different primary antibodies, and wherein the secondary antibody has a detectable label; and
    detecting the detectable label.

6. The method of claim 1, wherein the protein components of the sample are separated by charge and the method is a method of detecting and/or discriminating between the charge variants of the antibody of interest.

7. The method of claim 1, wherein the protein components of the sample are separated by molecular weight and the method is a method of detecting and/or discriminating between the size variants of the antibody of interest.

8. The method of claim 1, wherein the sample comprises one or more additional antibodies of interest.

9. The method of claim 8, wherein the one or more additional antibodies of interest are detected.

10. The method of claim 1, further comprising determining a relative or absolute amount of the size or charge variants of the antibody in the sample.

11. The method of claim 1, wherein the antibody of interest comprises a bispecific antibody.

12. The method of claim 4, wherein the detectable label comprises a chemiluminescent, a fluorescent label or a bioluminescent label.

13. The method of claim 1, wherein the sample includes an internal standard.

14. The method of claim 1, wherein the immobilizing comprises photo-immobilizing, chemically immobilizing, or thermally immobilizing.

15. The method of claim 1, wherein the one or more capillaries comprise a separation matrix.

16. The method of claim 15, wherein the separation matrix comprises carrier ampholytes.

17. The method of claim 15, wherein the separation matrix comprises a sieving matrix configured to separate proteins by molecular weight.

18. The method of claim 1, wherein the two or more primary antibodies comprise at least one antibody that specifically binds a light chain of the antibody of interest and at least one antibody that specifically binds a heavy chain of the antibody of interest.

* * * * *